United States Patent [19]

Knab

[11] 4,062,274
[45] Dec. 13, 1977

[54] EXHAUST SYSTEM FOR BONE CEMENT

[76] Inventor: James V. Knab, 2916 Hall St. SE., Grand Rapids, Mich. 49506

[21] Appl. No.: 693,193

[22] Filed: June 7, 1976

[51] Int. Cl.$^2$ ............................................. F23J 11/00
[52] U.S. Cl. .................. 98/115 R; 128/1 R; 417/12
[58] Field of Search ......... 128/1 R; 98/115 R, 115 K, 98/115 LH, 116, 119; 417/12

[56] References Cited

U.S. PATENT DOCUMENTS

| | | | |
|---|---|---|---|
| 879,463 | 2/1908 | Hansen | 98/115 K |
| 2,331,876 | 10/1943 | Walpole | 98/115 R |
| 3,479,947 | 11/1969 | Myers | 98/116 |
| 3,814,542 | 6/1974 | Iglesias et al. | 417/12 |

Primary Examiner—Ronald C. Capossela
Attorney, Agent, or Firm—Leydig, Voit, Osann, Mayer & Holt, Ltd.

[57] ABSTRACT

An exhaust system for evacuating the toxic fumes produced when mixing bone cement in a surgical operating room. A fan unit located within a vacuum plenum draws fume-laden air from a hood under which the bone cement is mixed, and exhausts the fume-laden air into a safe external atmosphere. A short interval timer is provided so that the system may be switched on by a non-sterile member of the operating team and thereafter automatically turned off. The capacity of the fan is relatively large as compared to the area of the hood so that all of the fumes are effectively exhausted during the relatively short cycle of operation of the system and are substantially diluted with air so as not to create a polluting effect of the external atmosphere to which the effluent is exhausted. A barometric damper located between the fan and the external atmosphere prevents the external atmosphere from entering the operating room when the fan is not in operation.

6 Claims, 7 Drawing Figures

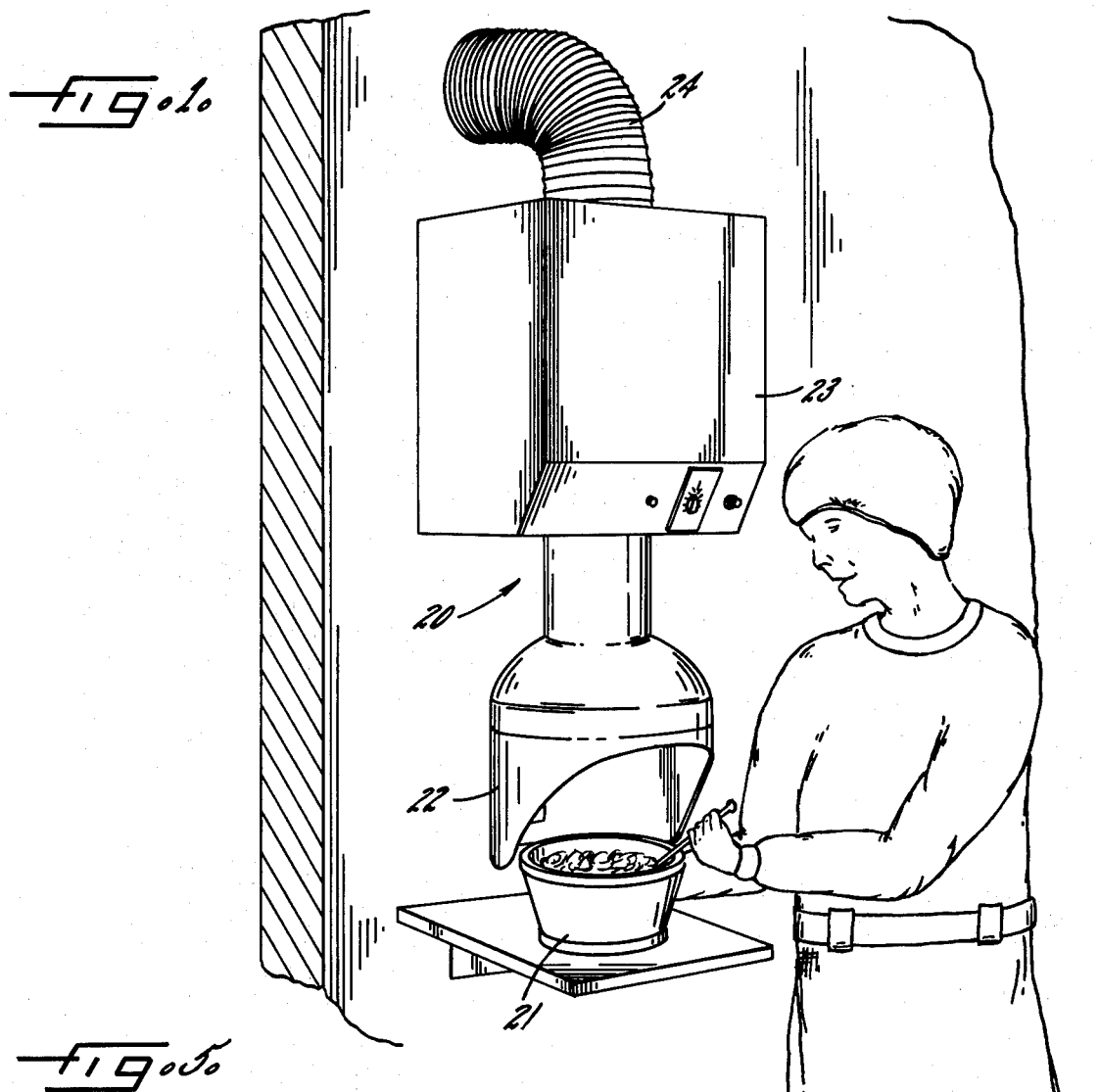
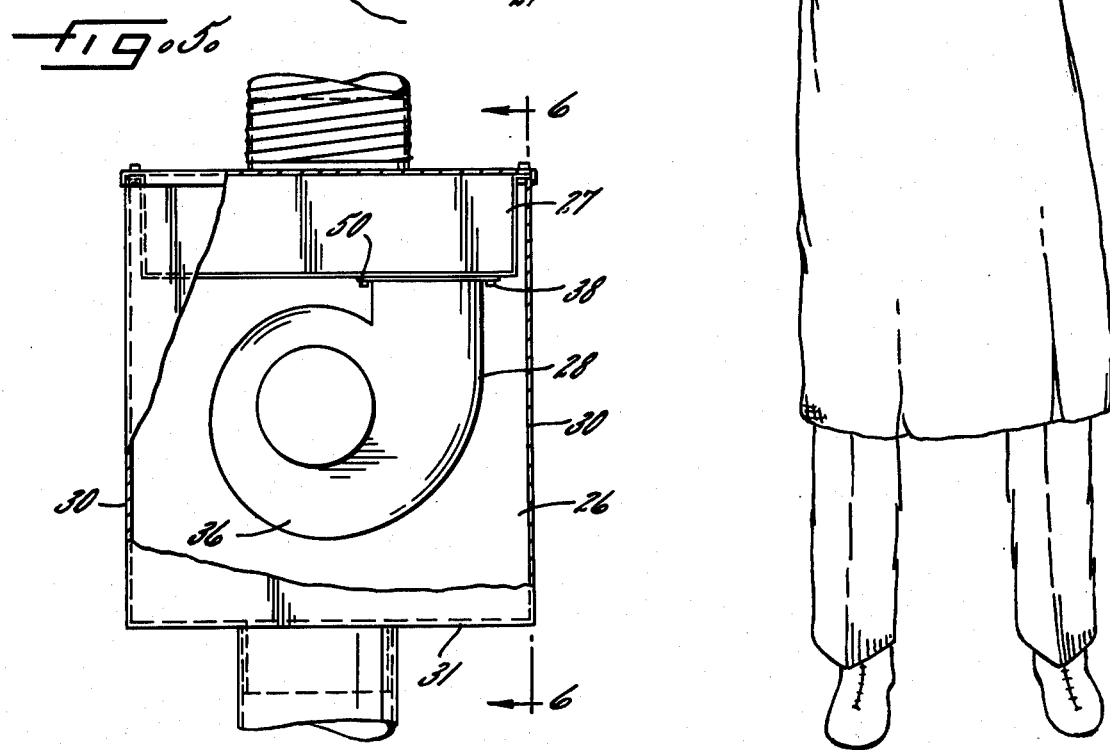

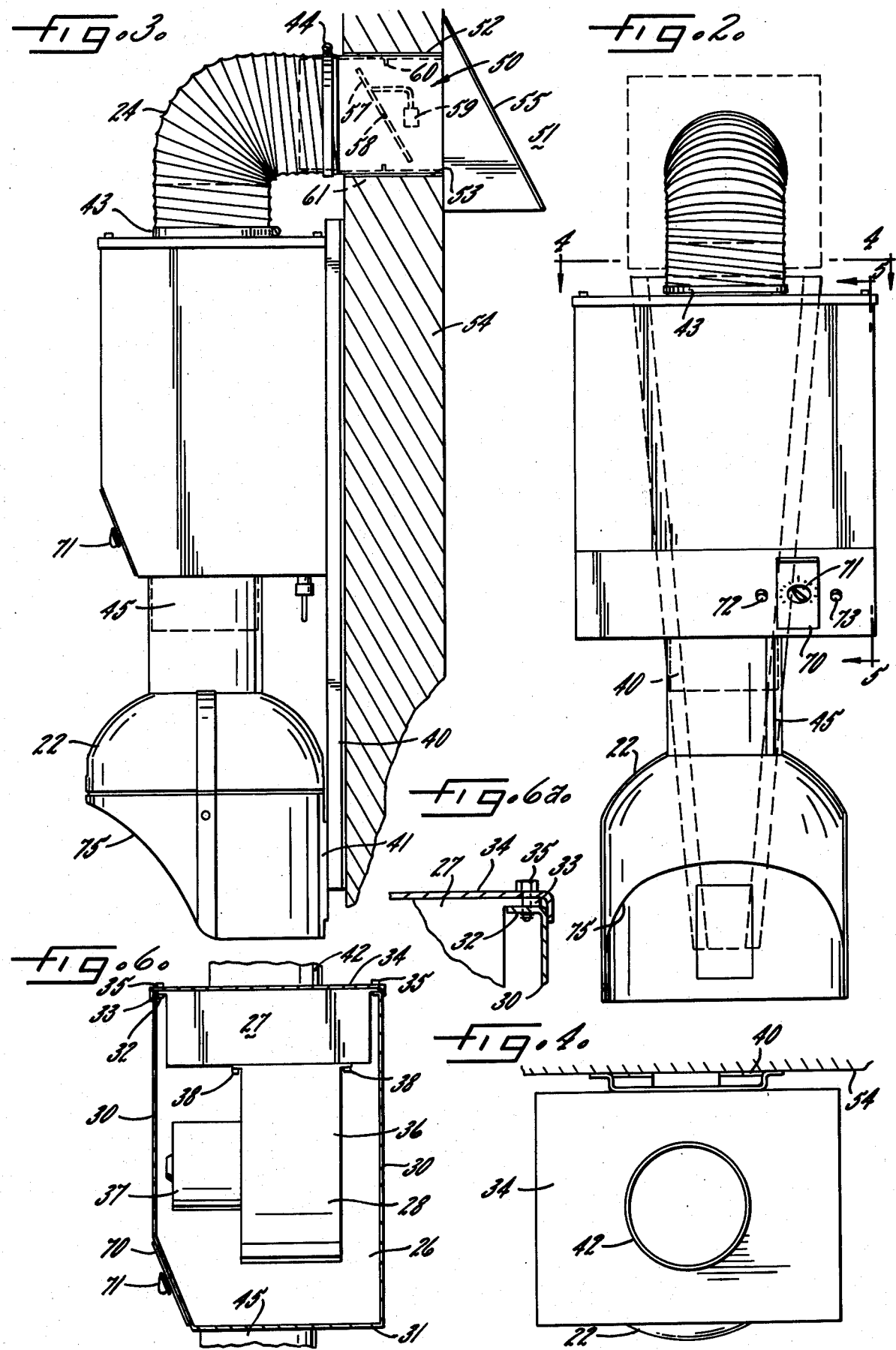

EXHAUST SYSTEM FOR BONE CEMENT

DESCRIPTION OF THE INVENTION

The present invention relates to fume exhaust systems, and more particularly, to exhaust systems for evacuating the toxic fumes produced when mixing bone cement in surgical operating rooms.

During orthopedic surgical operations, it is common practice to mix in the operating room immediately prior to use the bone cement that is to be employed during the operation. The most common type of bone cement consists of a methyl methacrylate powder which, when mixed with its companion liquid monomer, causes an exothermic reaction generating methyl methacrylate monomer fumes. Such fumes are highly toxic and can be harmful to the nurse who mixes the cement, as well as others in the operating room if permitted to escape into the environment of such room.

While hooded exhaust systems have long been known for removing undesirable fumes, present hooded exhaust systems have not been particularly well suited for use in operating rooms. For example, since the fumes from the bone cement must be removed as the cement is being mixed, present systems often are unable to effectively channel and remove all fumes without the use of relatively large vacuum motors. Such high capacity vacuum motors not only are noisy during the operation so as to create an annoyance to the patient or operating team, but they remove such large volumes of air from the operating room, particularly if used for a prolonged period, that they tend to create a negative pressure within the room which will draw in contaminants from the outside. This is particularly undesirable since most operating rooms are designed with ventilating systems adapted to create a slight positive pressure within the room to prevent contaminants from entering such as, through duct work, or under doors, etc.

It is an object of the present invention to provide an exhaust system adapted to more effectively remove from the operating environment noxious fumes emitted during mixing of bone cement without significantly affecting the desired positive pressure within the operating room.

Another object is to provide an exhaust system as characterized above that is adapted to quickly remove the noxious fumes and then automatically turn off the exhaust fan so as to prevent excessive removal of air from the operating room.

A further object is to provide an exhaust system of the above kind which has a hood that is adapted to more effectively channel the toxic fumes out of the operating room but which permits the nurse to easily mix the cement within the hooded area.

Yet another object is to provide such an exhaust system which draws relatively large quantities of air for substantially diluting the toxic fumes so as to permit the effluent to be exhausted without polluting the external atmosphere.

Still another object is to provide an exhaust system of the foregoing type that is adapted for quieter operation.

Yet another object is to provide an exhaust system which may be conveniently mounted on a wall with the hood being conveniently positionable at a desired elevation.

Other objects and advantages of the invention will become apparent upon reading the foregoing detailed description and upon reference to the drawings, in which:

FIG. 1 is a perspective view of an illustrative exhaust system embodying the present invention, being used to exhaust the toxic fumes generated from bone cement being mixed by a member of a surgical team;

FIG. 2 is an enlarged front elevation of the exhaust system shown in FIG. 1;

FIG. 3 is a side elevation of the exhaust system shown in FIG. 1;

FIG. 4 is a top view of the exhaust system taken in the plane of line 4—4 of FIG. 2;

FIG. 5 is a fragmentary section of the exhaust fan housing taken in the plane of line 5—5 in FIG. 2; and FIGS. 6 and 6a are fragmentary and enlarged fragmentary sections taken in the plane of line 6—6 in FIG. 5.

While the invention is susceptible of various modifications and alternative constructions, a certain illustrative embodiment has been shown in the drawings and will be described below in detail. It should be understood, however, that there is no intention to limit the invention to the particular form disclosed herein, but on the contrary, the intention is to cover all modifications, alternative constructions and equivalents falling within the spirit and scope of the invention.

Referring more particularly to FIG. 1 of the drawings, there is shown an illustrative exhaust system 20 mounted in an operating room and being used by a member of a surgical team to remove the toxic fumes from bone cement as it is being mixed within a bowl 21. The bone cement, as indicated previously, generally is a methyl methacrylate compound comprising a mixture of polymethyl methacrylate and methyl methacrylate styrene copolymer which is mixed with a liquid monomer to form a cement for use during the operation. The cement generally is mixed and kneaded for three to four minutes by a nurse or other member of the surgical team during which time the exothermic reaction resulting from the mixture emits highly toxic methyl methacrylate monomer fumes. The mixing bowl 21 is of a conventional stainless steel type.

The exhaust system 20 includes a hood 22, a vacuum plenum and motor housing 23 located immediately above the hood for creating a vacuum within the confines of the hood 22, and an exhaust conduit 24, leading from the vacuum housing 23. The exhaust conduit 24, which in the illustrated embodiment is in the form of a length of corrugated tubing, may be connected to an aperture in the wall of the operating room leading to the outside atmosphere, or alternatively may be connected to the ventilating duct work of the operating room which in turn will carry the exhausted air away from the operating room and to the outside environment.

The vacuum plenum and motor housing 23 is generally rectangular in configuration, and as shown in FIGS. 5 and 6, actually contains two sub-chambers 26, 27, with the sole means of communication between such sub-chambers being a fan unit 28. The lower chamber 26 is enclosed within vertical and bottom walls 30, 31, respectively, of the plenum 23, the vertical walls 30 being flanged at their upper portion 32 to provide a seat for the upper chamber assembly 27. The upper chamber 27 is generally rectangular in configuration and has flanges 33 mating the flanges of the vertical walls so that it may rest thereupon. The upper chamber is sealed by a cover 34 which may be bolted as at 35 through the flanges 33 of the chamber 27 into the flanges 32 of the vertical walls 30 thereby providing a rigid unit.

The fan unit 28 is of the centrifugal type including a centrifugal blower 36 driven by a motor 37, the motor being mounted directly on the fan casing. The fan 36 is affixed to the upper chamber 27 as by bolts 38. Using this arrangement the fan unit is readily serviced by removing the bolts 35 and the cover 34, after which the fan and upper chamber 27 may be simply lifted from the enclosure.

Forming a base for the assembly is a tapered channel member 40 which is affixed to the vacuum plenum housing 23 such as by welding. The member 40 is preferably formed of a channel for rigidity, and is tapered as shown in FIG. 2 for aestetic reasons so as to be hidden behind the hood 22. Apertures are provided in the flange members of the channel 40 for bolting the assembly to the wall. The hood 22 includes a flattened seat portion 41 for resting against the channel member 40 thereby to stabilize the hood.

Ascending from the cover 34 is a cylindrical sleeve 42 which forms the output of the upper chamber 27. A length of corrugated tubing 24 has its first end fitted over the sleeve 42 and is secured in place such as by circular clamp 43. The other end of the tubing 24 is attached by a similar clamp 44 to the outlet damper assembly to be described in detail below.

The housing 26 includes a depending cylindrical sleeve 45 forming a seat for the hood unit 22. The hood, in turn, includes an upper cylindrical sleeve 46 which closely mates the sleeve 45 when slid thereover so that no clamping is required. The hood defines a mixing zone under which the bowl is placed for mixing of the cement. In this arrangement, the hood may be adjusted over a limited range both vertically and rotationally to suit the requirements of the particular user.

Turning to FIG. 3, there is shown a barometric damper assembly generally indicated at 50 interposed between the exhaust tubing 24 and an external area 51 through which the fumes are exhausted. As noted above the area 51 may be the ventilating system of the hospital, or may simply be the outside atmosphere. The damper 50 in this case is housed within a sleeve 52 which fits within an aperture 53 in the wall 54. Preferably a screen 55 is interposed between the damper 50 and the external atmosphere 51 to prevent entry of foreign matter into the system.

The barometric damper 50 is effective to prevent backflow of air from the external atmosphere into the hood, and thereby into the operating room, when the flow is not operating. Such damper includes a baffle plate 57 arranged to pivot about an axis 58 and including a weighted member 59 for urging such damper into the closed position against stops 60, 61. With the fan turned off, the damper is urged by the weight against the stops, sealing the exhaust system from the external atmosphere 51. However, when the fan is operated, creating a positive pressure within the exhaust conduit 24, such pressure overrides the force exerted on the damper by the weight 59, thereby blowing the damper open and allowing the fumes to be exhausted. The damper is adjusted by means of appropriately selecting the weight 59 such that the slight positive pressure within the operating room will not open the damper, but such that the pressure created by operation of the fan will open such damper allowing the relatively free flow of exhaust.

According to an important feature of the invention, short interval timer means are provided for controllably establishing the operating period of the fan unit. In the illustrated embodiment, a timer 70 includes a knob 71 adapted to select the on time, such on time being adjustable between 1 and 10 minutes. An indicator light 72 is provided which glows while the fan is operating, clearly indicating to anyone in the operating room that the unit is exhausting air. A fuse 73 of appropriate capacity protects the motor circuit.

Because the nurse mixing the bone cement must have sterile hands, a second person, commonly termed the circulating nurse, usually is required to operate the controls. Using the exhaust system of the present invention, the circulating nurse need attend to the system only once, turning the system on and establishing the operating interval thereof. As a result, when the bone cement is mixed and is ready for use, and the operating team turns its attention to applying the cement to the patient, no further attention is required for turning the system off. In addition, once the timer is set, completion of a cycle not only turns the system off, but also serves to signal or remind the nurse that the cement is ready for use. It will be understood that if the system were allowed to run for any significant period after mixing of the cement, air would be continually withdrawn from the operating room in a manner which is not only purposeless, but actually detrimental in that it might affect the positive pressure maintained within the operating room.

The shape of the hood 22 is preferably domed as shown in the illustrated embodiment and includes a cutout portion 75 sufficient in size to allow the nurse to mix and view the cement while mixing, but not so large as to allow fumes to escape into the operating room. Preferably the cutout 75 is in the form of a continuous curve, offering maximum access to the underside of the hood while assuring that the noxious fumes are completely exhausted.

In keeping with the invention, the capacity of the fan unit is selected to be relatively high as compared to the area of the hood so as to effectively exhaust all of the noxious fumes. This feature is allowed by the automatic turn off of the system such that the high capacity fan is operated when needed, but turns off after the need for it ceases. In the illustrated embodiment, a fan is used which is capable of delivering about 400 cfm. Preferably, the capacity of the fan when installed in the illustrated environment should be in the range between 350 and 450 cfm. It has been found that because of the inherent back pressure of the system, a fan of somewhat larger design capacity, such as on the order of 525 cfm, may be required to draw and deliver an air flow within the desired range.

The fumes generated upon mixing of the bone cement are highly volatile and tend to disperse nearly instantaneously through the atmosphere of the operating room. The exhaust system of the present invention, with its relatively high air delivery capabilities, is effective to draw substantially all of the fumes into the hood and direct them through the exhaust plenum. If a fan of lower rating were utilized, significant portions of the toxic fumes might escape into the atmosphere of the room. On the other hand, if the rating were too high, excessive air would be withdrawn from the operating room without added benefit. In designing an exhaust system according to the present invention, several factors may be considered in determining the size of the fan unit. These factors include the size of the operating room, the estimated mixing time for the cement (usually between 3 and 7 minutes), and the total amount of air that may be removed from the room during the mixing time before the positive pressure in the room is offset. As indicated previously, however, the air flow generally need not exceed 450 cfm for achieving substantially complete removal of the toxic fumes, while 350 cfm is a minimum rate that should be established to insure adequate fume removal.

It will be appreciated that by reason of the relatively high air delivery capability of the system the toxic fumes drawn into the hood are substantially diluted with air prior to exhaust of the effluent to the external atmosphere so as to substantially eliminate or minimize the polluting effect on the atmosphere. In the illustrated embodiment in which which the fan unit draws about 400 cfm, it has been found that the effluent exhausted from the system has less than one part per million toxicity.

In operation, with the bone cement mixing bowl in place under the hood 22 the fan may be energized to create a significant vacuum in the chamber 26 which quickly draws air and substantially all of the fumes emanated during mixing of the cement through the hood 22 and into the chamber 26. The air and toxic fumes are then directed into the upper chamber 27 and through exhaust conduit 24 opening the damper plate 57 to permit passage to external atmosphere. After the predetermined interval of operation as set by the timer 70, which is set for the desired mixing time, the system will automatically shut off. Upon shut-off of the fan, the damper baffle 57 will automatically return to its closed position.

From the foregoing, it can be seen that the fumes generated during mixing of bone cement are quickly and reliably exhausted from the operating room by the exhaust system of this present invention. Furthermore, the exhaust system operates a minimum amount of time so as not to be an annoyance to the operating team and does not materially affect a positive pressure condition desired for the room.

What is claimed is:

1. An exhaust system for evacuating toxic fumes produced when mixing bone cement from an operating room to an external atmosphere comprising in combination, a vacuum plenum, an exhaust hood affixed to the vacuum plenum and defining a mixing zone, said hood having an aperture at a lower front portion thereof for allowing access to said mixing zone for mixing of bone cement directly under said hood, an exhaust conduit connecting the vacuum plenum to the external atmosphere, fan means within the plenum for drawing air and fumes emanated during mixing of said cement through the hood into the plenum and directing it out of the exhaust conduit and into the external atmosphere, said fan means being operable to direct an air flow through said system of more than 350 cubic feet per minute but less than an amount that would create a negative pressure in the operating room for drawing substantially all of the toxic fumes generated during mixing of said bone cement into said hood and plenum and diluting said fumes in said air flow such that the effluent exhausted into the external atmosphere has less than about one part by million toxicity, and timer means for establishing an interval of operation of said fan means to automatically limit the amount of air exhausted by the vacuum system.

2. The exhaust system as set forth in claim 1 in which said fan is operable to direct an air flow of about 400 cfm through said system.

3. The exhaust system as set forth in claim 1 wherein the exhaust hood includes a domed portion connected to an upstanding sleeve portion, said upstanding sleeve portion mating a depending cylindrical sleeve at the underside of said vacuum plenum, said upstanding sleeve portion closely fitting said depending sleeve so that said hood may be adjusted vertically and rotationally upon said depending sleeve.

4. The exhaust system as set forth in claim 3 including means interposed between the exhaust conduit and the external atmosphere for preventing backflow of external atmosphere into the operating room when the fan is not in operation.

5. The exhaust system as set forth in claim 4 in which said back flow preventing means is a barometric damper.

6. The exhaust system as set forth in claim 5 wherein said barometric damper includes a pivotable damper blade having a closed position sealing the external atmosphere from the exhaust system, means urging said damper blade into said closed position, said damper blade urging means being adapted to be overridden by air exhausted through said exhaust conduit when said fan is in operation, thereby automatically allowing the exhaust of air when the system is operated, but sealing said system when not operated.

* * * * *